United States Patent
Nguyen et al.

(10) Patent No.: US 7,262,159 B2
(45) Date of Patent: Aug. 28, 2007

(54) ODOR ELIMINATION COMPOSITION FOR USE ON SOFT SURFACES

(75) Inventors: Peter N. Nguyen, Racine, WI (US); Cary E. Manderfield, Racine, WI (US); Maciej K. Tasz, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 11/313,297

(22) Filed: Dec. 20, 2005

(65) Prior Publication Data

US 2007/0142264 A1    Jun. 21, 2007

(51) Int. Cl.
C11D 1/835 (2006.01)
C11D 3/44 (2006.01)

(52) U.S. Cl. ............ 510/287; 510/289; 510/293; 510/295; 510/308; 510/329; 510/330; 510/341; 510/342; 510/356; 510/384; 510/421; 510/432; 510/504; 510/515; 510/524; 510/525

(58) Field of Classification Search ............ 510/287, 510/289, 293, 295, 308, 329, 330, 341, 342, 510/356, 384, 421, 432, 504, 515, 524, 525

See application file for complete search history.

(56) References Cited

U.S. PATENT DOCUMENTS

| | | |
|---|---|---|
| 3,160,555 A | 12/1964 | Hamill et al. |
| 3,567,118 A | 3/1971 | Shepherd et al. |
| 3,943,242 A | 3/1976 | Fogel et al. |
| 3,993,250 A | 11/1976 | Shure |
| 4,048,369 A | 9/1977 | Johnson |
| 4,078,055 A * | 3/1978 | Naganuma et al. ......... 424/76.6 |
| 4,184,985 A | 1/1980 | Scheuermann et al. |
| 4,202,800 A * | 5/1980 | Ciko et al. ............... 510/325 |
| 4,275,054 A * | 6/1981 | Sebag et al. .............. 424/65 |
| 4,294,821 A * | 10/1981 | Neumiller ............... 424/45 |
| 4,304,679 A * | 12/1981 | Hooper et al. ............ 424/402 |
| 4,511,486 A * | 4/1985 | Shah ..................... 134/42 |
| 4,540,721 A | 9/1985 | Staller |
| 4,606,842 A | 8/1986 | Keyes et al. |
| 4,652,389 A | 3/1987 | Moll |
| 4,690,779 A | 9/1987 | Baker et al. |
| 4,816,220 A * | 3/1989 | Roychowdhury ............ 422/5 |
| 4,880,557 A | 11/1989 | Ohara et al. |
| 4,883,651 A | 11/1989 | Meyer |
| 4,906,462 A | 3/1990 | Miki et al. |
| 4,934,609 A | 6/1990 | Lindauer et al. |
| 4,938,416 A | 7/1990 | Bertrand et al. |
| 5,094,761 A | 3/1992 | Trinh et al. |
| 5,102,564 A | 4/1992 | Gardlik et al. |
| 5,126,068 A | 6/1992 | Burke et al. |
| 5,219,890 A | 6/1993 | Boucher |
| 5,380,707 A | 1/1995 | Barr et al. |
| 5,444,094 A | 8/1995 | Malik et al. |
| 5,578,563 A | 11/1996 | Trinh et al. |
| 5,593,670 A | 1/1997 | Trinh et al. |
| 5,663,134 A | 9/1997 | Trinh et al. |
| 5,668,097 A | 9/1997 | Trinh et al. |
| 5,670,475 A | 9/1997 | Trinh et al. |
| 5,714,137 A | 2/1998 | Trinh et al. |
| 5,783,544 A | 7/1998 | Trinh et al. |
| 5,939,060 A | 8/1999 | Trinh et al. |
| 5,942,217 A | 8/1999 | Woo et al. |
| 5,955,093 A | 9/1999 | Woo et al. |
| 5,955,414 A | 9/1999 | Brown et al. |
| 5,968,404 A | 10/1999 | Trinh et al. |
| 5,997,759 A | 12/1999 | Trinh et al. |
| 6,001,343 A | 12/1999 | Trinh et al. |
| 6,033,679 A | 3/2000 | Woo et al. |
| 6,034,261 A * | 3/2000 | Matsunaga et al. ......... 558/110 |
| 6,077,318 A | 6/2000 | Trinh et al. |
| 6,080,387 A | 6/2000 | Zhou et al. |
| 6,146,621 A | 11/2000 | Trinh et al. |
| 6,177,070 B1 | 1/2001 | Lynch |
| 6,248,135 B1 | 6/2001 | Trinh et al. |
| 6,284,231 B1 | 9/2001 | Trinh et al. |
| 6,395,236 B1 * | 5/2002 | Stewart ................. 422/123 |
| 6,451,065 B2 | 9/2002 | Trinh et al. |
| 6,454,876 B1 | 9/2002 | Ochomogo et al. |
| 6,471,974 B1 | 10/2002 | Rees et al. |
| 6,482,392 B1 | 11/2002 | Zhou et al. |
| 6,528,472 B2 | 3/2003 | Charaf et al. |
| 6,573,233 B1 * | 6/2003 | Altmann et al. ............ 510/470 |
| 6,680,289 B1 * | 1/2004 | Woo et al. ................. 510/470 |
| 6,767,507 B1 | 7/2004 | Woo et al. |

(Continued)

FOREIGN PATENT DOCUMENTS

WO    WO2006/023858 A1    3/2006

*Primary Examiner*—Charles Boyer
(74) *Attorney, Agent, or Firm*—Miller, Matthias & Hull

(57) ABSTRACT

A method and composition for deodorizing soft surfaces such as carpeting and upholstery are disclosed. The method includes the spraying of a liquid composition on a soft surface and allowing the composition to absorb into the soft surface, form liquid agglomerations within the soft surface to the agglomerations can make contact with malodorants disposed within the soft surface. The composition comprises an active ingredient that is a liquid at room temperature with a vapor pressure of less than 0.0035 mmHg at room temperature. For example, the active ingredient can be triethylene glycol. Other ingredients that contribute to agglomeration formation include ethanol, water, fragrance and a combination of at least one nonionic and at least one ionic surfactant.

19 Claims, No Drawings

U.S. PATENT DOCUMENTS

| | | |
|---|---|---|
| 6,780,403 B1 * | 8/2004 | Yamashita et al. ............ 424/65 |
| 6,794,346 B2 | 9/2004 | Wick et al. |
| 6,814,088 B2 | 11/2004 | Barnabas et al. |
| 6,867,174 B2 | 3/2005 | Ramirez, Jr. et al. |
| 6,943,140 B2 | 9/2005 | Ashton et al. |
| 7,082,951 B2 | 8/2006 | Barnabas et al. |
| 7,094,741 B2 | 8/2006 | Barnabas et al. |
| 2002/0039566 A1 * | 4/2002 | Triplett et al. ............. 424/76.1 |
| 2002/0132861 A1 * | 9/2002 | Uchiyama et al. .......... 516/198 |
| 2003/0027737 A1 | 2/2003 | Evers |
| 2003/0044309 A1 | 3/2003 | Hernandez et al. |
| 2003/0045439 A1 | 3/2003 | Evers |
| 2003/0145965 A1 | 8/2003 | Anderson et al. |
| 2003/0162678 A1 | 8/2003 | Ashton et al. |
| 2003/0191034 A1 | 10/2003 | Woo et al. |
| 2003/0216488 A1 * | 11/2003 | Uchiyama et al. .......... 523/102 |
| 2004/0147426 A1 * | 7/2004 | Bettiol et al. ............... 510/475 |
| 2004/0213750 A1 | 10/2004 | Bennett et al. |
| 2005/0003990 A1 | 1/2005 | Smith et al. |
| 2005/0089540 A1 | 4/2005 | Uchiyama et al. |
| 2005/0100520 A1 * | 5/2005 | Hagura et al. ................ 424/65 |
| 2005/0196374 A1 | 9/2005 | Ueda et al. |
| 2005/0202991 A1 | 9/2005 | De Dominicis et al. |
| 2005/0227897 A1 | 10/2005 | Nelson et al. |
| 2006/0228250 A1 * | 10/2006 | Brown et al. .................. 422/5 |

* cited by examiner

ODOR ELIMINATION COMPOSITION FOR USE ON SOFT SURFACES

BACKGROUND

1. Technical Field

An improved liquid formulation is disclosed which effectively removes odors embedded in soft surfaces such as carpeting and upholstery. The improved formulation makes use of triethylene glycol and a combination of nonionic and ionic surfactants, one of which has bactericidal properties.

2. Description of the Related Art

It has been known to use certain glycols in aerosols or vapor forms to sanitize air in a room by killing airborne bacteria. One particular glycol, triethylene glycol ("TEG"), has been found particularly effective for sanitizing air when delivered via an aerosol spray. The commercially successful OUST® air sanitizer products utilize a mixture that contains about 6 wt % TEG. A non-aerosol application of TEG for disinfecting air is enclosed in U.S. Pat. No. 5,591,395, commonly assigned with the present application. TEG has also been used as an air treatment for tobacco smoke. See U.S. Pat. No. 6,395,236.

Triethylene glycol has the following structure:

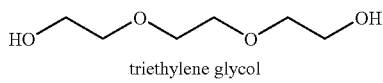

triethylene glycol

TEG is a colorless, odorless, non-volatile and hygroscopic liquid. It is characterized by two hydroxyl groups along with two ether linkages which contribute to its high water solubility, hygroscopicity and its ability to neutralize airborne odor-causing bacteria. TEG can be prepared commercially by the oxidation of ethylene at high temperatures in the presence of a silver oxide catalyst, following by hydration of the ethylene oxide to yield mono-, di-, tri- and tetra-ethylene glycol products. TEG has a low toxicity.

Until now, the treatment and removal of odor-causing substances from soft surfaces such as clothing, drapes, bedding, carpeting and upholstery utilize very different mechanisms. One strategy uses water-soluble cyclodextrins for odor control as discussed extensively in U.S. Pat. Nos. 5,760,475, 6,077,318, 6,248,135 and 6,451,065. These patents all teach the use of water-soluble cyclodextrins in combination with water-soluble metallic salts.

Cyclodextrins have a toroidal structure, the interior of which is hydrophobic. The exterior of this toroid structure is hydrophilic thereby rendering them water-soluble. It has been found that hydrophobic odor-causing compounds enter the hydrophobic interior of a cyclodextrin toroid and form a stable complex with the cyclodextrin structure due to the interplay of Van der Waals forces, the effects of hydrogen bonding and the common hydrophobicity of the cyclodextrin interior and odor-causing molecule. By forming stable complexes with odor-causing molecules, cyclodextrins keep the molecules out of the air thereby reducing the odor caused thereby. Water-soluble metallic salts may be combined with the cyclodextrins to absorb amines and sulfur-containing compounds.

A second approach utilizes water soluble/dispersible polymers as taught in U.S. Pat. No. 6,454,876. In contrast to cyclodextrins, which entrap or cage the odor-causing molecule within the cyclodextrin toroid as discussed above, the water soluble/dispersible polymer of the '876 patent entraps the odor-causing molecule by forming a film that blankets the odor-causing molecule. The film is formed as the solvent or carrier evaporates. Thus, the residual polymer film provides a barrier to contain the odor-causing material in the soft surface thereby preventing it release to the ambient environment and detection by the consumer's sense of smell.

Both the cyclodextrin and film-forming polymer products leave a residue after the solvent or carrier evaporates. Further, neither cyclodextrins nor film-forming polymers have any anti-microbial properties.

Other more drastic measures at treating odor-causing molecules trapped in carpeting, upholstery and clothing involve the use of enzymes or detergents to remove the odor-causing molecules. In the case of upholstery and carpeting, professional services or the renting of special machinery is often required.

Therefore, there is a need for an improved means for removing odors in soft surfaces that are not easily washable, i.e., carpeting and upholstery. What is needed is an improved liquid application that may be sprayed onto carpeting or upholstery, that will not discolor or form a film or residue on the carpeting or upholstery, and that will effectively deliver active odor-neutralizing ingredients to odor-causing molecules trapped in the carpeting or upholstery.

SUMMARY OF THE DISCLOSURE

In satisfaction of the afore noted needs, a method and a composition are disclosed for eliminating odors embedded in soft surfaces such as carpeting, upholstery, clothing, bed linens, etc.

In an embodiment, a disclosed method for deodorizing soft surfaces comprises spraying a liquid formula on a soft surface, wherein the formula comprises an active ingredient that is a liquid at room temperature and that has a vapor pressure at room temperature of less than 0.0035 mmHg, and allowing the formula to absorb into the soft surface and make contact with an odor causing material disposed within the soft surface.

The active ingredient that is a liquid at room temperature and that has a vapor pressure at room temperature of less than 0.0035 mmHg at room temperature may be a glycol or another suitable material, one of which is triethanolamine (TEA). Other materials for use at the active ingredient will be apparent to those skilled in the art upon reading this disclosure.

In a refinement, the active ingredient is a glycol selected from the group consisting of triethylene glycol (TEG), dipropylene glycol, propylene glycol and combinations thereof. Triethanolamine is also an option for the active ingredient.

In an embodiment, a disclosed method for deodorizing soft surfaces comprises spraying a liquid formula on a soft surface wherein the liquid formula comprises an active ingredient that may be a glycol selected from the group consisting of triethylene glycol (TEG), dipropylene glycol, and propylene glycol or another ingredient having a vapor pressure at room temperature of less than 0.0035 mmHg, and allowing the formula to absorb into the soft surface and make contact with an odor causing material disposed within the soft surface.

In such a method, agglomerations of the glycol or other active ingredient, carrier, fragrance and surfactant form in the soft surface. When odor-causing materials engage these agglomerations, the odor-causing materials are dissolved into the agglomeration thereby reducing the partial vapor pressure of the odor-causing material and the odor caused thereby. As the glycol or other active ingredient remains in a liquid form, no dried residue is apparent or visible.

In a refinement, the formula further comprises water and a low molecular weight alcohol such as a short chain monohydric alcohol. In a further refinement of this concept, the alcohol is selected from the group consisting of ethanol, isopropanol, butanol and propanol. Ethanol is currently preferred due to its low cost and acceptable odor. Additional co-solvents include glycol ethers such as glycol monoethyl ether and diethylene glycol butyl ether.

The alcohol and water both act as solvents or carriers and the alcohol reduces the drying time of the disclosed liquid formulation. Preferably, the alcohol is a minor component compared to that of water, with the water content ranging from about 75-95 wt % and the alcohol content ranging from about 1 to about 10 wt %, most preferably about 6 wt %.

In another refinement, the formula further comprises a plurality of surfactants. The surfactants may comprise a plurality of nonionic surfactants, a combination of nonionic and ionic surfactants, or, more specifically, a combination of nonionic and cationic surfactants. Amphoteric and zwitterionic surfactants may also be used.

In a further refinement of this concept, the plurality of surfactants includes at least one ionic surfactant and at least one nonionic surfactant. The surfactants used in the formula may also be known in others applications as emulsifiers and, for the purposes of this disclosure, the terms surfactant and emulsifier will be considered to be interchangeable as the common property of surfactants and emulsifiers, i.e., reducing surface tension, is the important function for purposes of this application. Combinations of nonionic surfactants have been found to be effective as well as combinations of nonionic and cationic surfactants.

In a refinement, the nonionic surfactant comprises a combination of an ether and a hydrogenated castor oil derivative. In a further refinement, the nonionic surfactants comprise a combination of polyglycol ether and an ethoxylated hydrogenated castor oil. In still a further refinement, polyglycol ether is a polyoxyethylene alkylether.

In another refinement, the ionic surfactant is a cationic surfactant. Preferably, the cationic surfactant is a quaternary ammonium salt. A benefit of using a quaternary ammonium salt is the anti-bacterial properties of these salts.

One disclosed formulation for carrying out the above-described method comprises: water; a short chain monohydric alcohol; a glycol selected from the group consisting of triethylene glycol (TEG), dipropylene glycol, propylene glycol, and combinations thereof or another material that is a liquid at room temperature and that has a vapor pressure at room temperature of less than 0.0035 mmHg at room temperature; fragrance; at least one nonionic surfactant, and at least one ionic surfactant. As noted above, dipropylene glycol and propylene glycol may be substituted for the currently preferred glycol, TEG. Also, as indicated, combinations of these glycols may be used.

In a refinement, the glycol may be present in an amount ranging from 0.5 to about 5 wt %. Most preferably, the glycol, which is preferably but not necessarily TEG, comprises about 1 wt % of the formulation.

In another refinement, the applied formulation comprises from about 1 to about 10 wt % low molecular weight monohydric alcohol or glycol ether, from about 0.5 to about 5 wt % glycol, from about 0.25 to about 0.75 wt % fragrance, from about 1 to about 2 wt % nonionic and ionic surfactants and, the remainder, water. The surfactant content can range from about 0.5 to about 2 wt %.

In a preferred embodiment the surfuctant combination comprises a hydrogenated castor oil derivative, a polyglycol ether; and a quaternary ammonium salt.

In one preferred embodiment, the formulation comprises from about 4 to about 8 wt % ethanol, from about 0.5 to about 1.5 wt % TEG, from about 0.5 to about 0.75 wt % fragrance, from about 0.5 to about 1.5 wt % nonionic surfactant, from about 0.1 to about 1 wt % cationic surfactant and, the remainder, water.

In a further refinement of this concept, the nonionic surfactants comprise a combination of a hydrogenated castor oil derivative and a polyglycol ether. In a further refinement, the ionic surfactant comprises a quaternary ammonium salt. In still a further refinement, the nonionic surfactants may include (1) a hydrogenated castor oil derivative, that includes glycerol and polyethylene glycol oxystearate, and (2) a polyglycol ether that is an ethoxylation product $C_{11}$ to $C_{15}$ linear secondary alkanols with ethylene oxide.

Other advantages and features of the disclosed methods and compositions will be described in greater detail below.

DETAILED DESCRIPTION OF THE PRESENTLY PREFERRED EMBODIMENTS

An improved odor reducing liquid for carpeting, upholstery and other soft surfaces is provided. The improved formulation delivers an active ingredient to odor-causing compounds or molecules embedded within soft surfaces thereby enabling active ingredient to come into contact with the odor-causing compounds and molecules. Without being bound to any particular theory, it is believed that the active ingredient, in combination with other materials of the formulation, form agglomerations within the soft surface. When an odor-causing material or molecule engages these agglomerations, the odor-causing material is dissolved into the agglomeration thereby reducing the partial vapor pressure of the odor-causing material to a level below what is needed to be detected by the human sense of smell. As the glycol or other active ingredient remains in a liquid form, the agglomerations remain as liquid agglomerations for an extended period of time and no dried residue is apparent or visible.

Also, when the disclosed formulations are applied to a soft surface, the malodor molecules adsorbed onto the soft surface are first dissolved in the liquid aqueous formulation before formation of the agglomerations. As the malodor molecules desorb from the soft surface, some of the molecules enter the gas phase rather than the applied aqueous phase. The degree to which a molecule will desorb from the soft surface preferentially into the gas phase will depend of the degree of solubility of the molecule in the aqueous phase. Molecules with good water solubility will transferred to the applied aqueous phase. Molecules with poor water solubility will desorb from the surface into the air.

Since the agglomeration mechanism for odor elimination is driven by solubility parameters, malodor molecules having poor water solubility are least likely go into the aqueous or polar solution and therefore most likely to desorb from the surface into the surrounding air. The formulations disclosed herein encourage this action for such malodorants. The disclosed formulations, which include a mixed solvent system, e.g. water/alcohol/glycol, can enhance the solubility of the malodor molecule in the applied product. The disclosed formulations offer a dual action odor elimination mechanism: desorption of malodor from the surface as well as increased solubility of malodor molecules in the applied product. Odors that are desorbed from the surface into the surrounding air can be removed from the home by other means such as natural air change, i.e. ventilation.

Molecules solubilized by the mixed solvent system will ultimately remain in the low volatile liquids, e.g. glycol or TEA and desorb from the residual film at a much slower rate. The degree to which malodor molecules will be taken up in the mixed solvent systems can be controlled by adjusting the solubility parameters of the mixed solvent system to more closely match the solubility parameters of the malodor molecules.

Certain odorous compounds such as thiols, amines, acids and sulfides will readily dissolve into the agglomerations which, by way of an example, can comprise a core of the active ingredient (i.e., the glycol or other liquid with a vapor pressure at room temperature of less than 0.0035 mmHg), carrier, fragrance and an outer portion that includes significant amounts of surfactant. Thus, the disclosed formulations do not mask odor-causing compounds and molecules; they keep them from being detected by reducing their vapor pressures.

Eight exemplary formulations are disclosed below. It should be noted that this disclosure is not limited to the particular seven formulations and acceptable ranges of the various ingredients are also set forth below.

EXAMPLE 1

| Wt % | Name/Formula | Function |
| --- | --- | --- |
| 92.325 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.25 | fragrance oil mixture (TAKASAGO RK-1428, outdoor) | fragrance |
| 0.2650 | PROTACHEM ™ CAH-60, hydrogenated castor oil (glycerol, polyethylene glycol oxystearate) | nonionic surfactant |
| 0.11 | SOFTANOL ™ 70, polyoxyethylene alkylether | nonionic surfactant |
| 100.00 | | |

EXAMPLE 2

| Wt % | Name/Formula | Function |
| --- | --- | --- |
| 92.325 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.25 | fragrance oil mixture (TAKASAGO RK-1428, outdoor) | fragrance |
| 0.2650 | PROTACHEM ™ CAH-60, hydrogenated castor oil (glycerol, polyethylene glycol oxystearate) | nonionic surfactant |
| 0.11 | TERGITOL ™ 15-s-7, polyglycol ether | nonionic surfactant |
| 100.00 | | |

EXAMPLE 3

| Wt % | Name/Formula | Function |
| --- | --- | --- |
| 91.45 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.15 | Agent 2248-14, quaternary ammonium salt | cationic surfactant |
| 100.00 | | |

EXAMPLE 4

| Wt % | Name/Formula | Function |
| --- | --- | --- |
| 91.2 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | Fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.50 | Agent 2248-14, quaternary ammonium salt | cationic surfactant |
| 100.00 | | |

EXAMPLE 5

| Wt % | Name/Formula | Function |
| --- | --- | --- |
| 91.2 | de-ionized water | solvent/carrier |
| 6.0 | isopropanol, $(CH_3)_2CHOH$ | solvent/carrier |
| 1.00 | TEA, triethanolamine $(HOCH_2CH_2)_3N$ | odor remover |
| 0.40 | fragrance oil mixture (TAKASAGO RK-1428, outdoor) | fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.50 | Agent 2248-14, quaternary ammonium salt | cationic surfactant |
| 100.00 | | |

EXAMPLE 6

| Wt % | Name/Formula | Function |
| --- | --- | --- |
| 91.2 | de-ionized water | solvent/carrier |
| 6.0 | isopropanol, $(CH_3)_2CHOH$ | solvent/carrier |
| 1.00 | Dipropylene glycol | odor remover |
| 0.40 | fragrance oil mixture (TAKASAGO RK-1428, outdoor) | fragrance |

-continued

| Wt % | Name/Formula | Function |
|---|---|---|
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.50 | Agent 2248-14, quaternary ammonium salt | cationic surfactant |
| 100.00 | | |

EXAMPLE 7

| Wt % | Name/Formula | Function |
|---|---|---|
| 90.6 | de-ionized water | solvent/carrier |
| 6.0 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | Fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.40 | Agent 2248-14, quaternary ammonium salt | cationic surfactant |
| 0.60 | nitrogen | propellant |
| 100.00 | | |

EXAMPLE 8

| Wt % | Name/Formula | Function |
|---|---|---|
| 71.2 | de-ionized water | solvent/carrier |
| 6.00 | ethanol, $CH_3CH_2OH$ | solvent/carrier |
| 1.00 | TEG, triethylene glycol $HO(CH_2)_2O(CH_2)_2O(CH_2)_2OH$ | odor remover |
| 0.40 | fragrance oil mixture (TAKASAGO RK-1428, outdoor) | Fragrance |
| 0.50 | PROTACHEM ™ CAH-60, hydrogenated castor oil (glycerol, polyethylene glycol oxystearate) | nonionic surfactant |
| 0.50 | TERGITOL ™ 15-s-7, polyglycol ether | nonionic surfactant |
| 0.40 | Agent 2248-14, quaternary ammonium salt | cationic surfactant |
| 20.00 | hydrocarbon propellant (LPG) | propellant |
| 100.00 | | |

Water and ethanol serve as carriers and co-solvents. The inclusion of ethanol, or an other short chain monohydric alcohol, provides for a faster dry time for the applied composition. Ethanol is also an excellent carrier and therefore assists in delivering the active ingredient to where it is needed. Additional co-solvents include glycol ethers such as glycol monoethyl ether and diethylene glycol butyl ether. The alcohol or glycol ether co-solvent should be present in the range of from about 1 to about 10 wt %.

Because the TEG is provided in a suitable carrier and because it will not quickly evaporate once it has impregnated a soft surface, the amount of TEG may be relatively low as compared at an aerosol air sanitizing formulation. Typically, an air sanitizing formulation will have about 6 wt % TEG; in this particular application, i.e., soft surfaces, the amount of TEG can be reduced to less than 5 wt %. In the examples above, the TEG comprises 1.0 wt % of the formulations. However, depending on the particular use or particular odors being treated, the TEG content can vary widely and could range from 0.5 wt % to 6.0 wt % or more. Examples 1-4 and 7-8 above, with their 1.0 wt % TEG content, are merely currently preferred embodiments.

TEG is not the only glycol that can be used. Dipropylene glycol (Example 6) and propylene glycol are also suitable. Further, an active ingredient that is a liquid at room temperature and that has a vapor pressure at room temperature of less than 0.0035 mmHg may be utilized.

Another alternative to TEG or another glycol is triethanolamine (TEA). See Example 5. Like TEG, TEA is a liquid at room temperature, has a low vapor pressure at room temperature ($3.6 \times 10^{-6}$ mmHg) and has a non-offensive odor.

The fragrances utilized can be obtained from Takashago International Corp., a Japanese corporation having an office at 4 Volvo Drive, Rockleigh, N.J. 07647 (http://www-.takashago.com). Of course, one skilled in the art will know that other suppliers of fragrances exist and this disclosure is not limited to the particular fragrances utilized herein. A preferred fragrance range is from about 0.25 to about 0.75 wt %.

Novel combinations of surfactant/emulsifiers are also utilized, Examples 1 and 2 utilize only nonionic surfactants in the form of a hydrogenated castor oils derivative and a polyglycol ether. The hydrogenated castor oil derivative is sold under the tradename PROTACUEM™ CAH-60 and the INCI/CTFA chemical name "PEG-60 hydrogenated castor oil." These materials can be obtained from Protameen Chemicals, Inc., 375 Minnisik Road, Totowa, N.J. 07511. The hydrogenated castor oil derivative may be a glycerol stearate, and if ethoxylated, may be a polyethylene glycol oxystearate.

The other nonionic surfactant or emulsifier utilized is either TERGITOL™ 15-S-7, which is a polyglycol ether. It is available from Sigma-Aldrich, P.O. Box 14508, St. Louis, Mo. 63718 as well as the Dow Chemical Co., 2030 Dow Center, Midland, Mich. 48674. Other sources of TERGITOL™ will be apparent to those skilled in the art. Another option for a nonionic surfactant is SOFTANOL™ 70, available from Nippon Shokubai of Osaka 541-0043, Japan. Other branched or linear, primary or secondary, polyethoxylated alcohols can be used as nonionic surfactants.

Thus, Examples 1 and 2 include only nonionic surfactants. While these examples provide an excellent mechanism for delivering the active ingredient (e.g., TEG) and fragrance to odor-causing molecules residing in soft surfaces, it has been surprisingly found that the combination of nonionic and ionic surfactants provides still improved utility. Thus, small amounts of a quaternary ammonium salt in the form of Agent 2248-14 are added in Examples 3 through 8. The combination of the quaternary ammonium salt with the nonionic surfactants provides improved penetrability and delivery of TEG to the problematic areas within carpeting, upholstery, bedding, drapes, etc. By using a combination of nonionic and cationic surfactants, the disclosed formulations and methods provide a means for delivering TEG to odor-causing molecules buried deep within upholstery or carpeting. Thus, the TEG can be effectively delivered to deeply embedded odor-causing materials such as pet urine or other problematic odors. Further, Agent 2248-14 and other quaternary ammonium salts have anti-microbial properties and therefore add a sanitization function to the disclosed formulations. The total surfactant content preferably ranges from about 0.50 to about 2 wt %.

The preferred quaternary ammonium salt (Agent 2248-14) is a mixture of alkyl dimethyl benzyl ammonium chloride and alkyl dimethyl ethyl benzyl ammonium chloride. It is sold by the Stepan Company, 22 Frontage Road, Northfield, Ill. 60093 (www.stepan.com) in a preparation that is 25 wt % alkyl dimethyl benzyl ammonium chloride, 25 wt % alkyl dimethyl ethyl benzyl ammonium chloride, 2-3 wt % ethanol and the remainder water.

A wide variety of ionic surfactants are available and quaternary ammonium salts are not the only possibility. While cationic surfactants are utilized in the form of quaternary ammonium salts, other cationic surfactants will be apparent to those skilled in the art without undue experimentation.

Aerosol formulations are provided in Examples 7 and 8, using nitrogen propellant and hydrocarbon propellant respectively.

Therefore, the disclosed method and compositions provide a new application for TEG, other glycols and other materials that are liquids at room temperature and that have a vapor pressure of less than 0.0035 mmHg at room temperature, as a malodor absorbent for soft surfaces. The use of TEG has been extended to treating odors embedded in soft surfaces such as carpeting and upholstery. When the composition is applied, a layer or an agglomeration is formed within the soft surface substrate in close proximity to the malodor sources. The odor-causing molecules come into contact with the agglomeration and dissolve in the agglomeration thereby reducing their effective vapor pressure. Many malodorous components (thiols, amines, acids, sulfites, etc.), have a very low air/solvent partition coefficients (Henry's constant), which confirms the broad-spectrum odor suppression capability of TEG and other glycols. In summary, the malodorous components have a greater affinity for TEG than air thus reducing the vapor pressure and perception by the human sense of smell.

The agglomerations or droplets formed by the active ingredient (TEG, dipropylene glycol, propylene glycol, or material with a vapor pressure of less than 0.0035 mmHg at room temperature), carrier, fragrance and surfactants have an inner portion or core where the active ingredient, fragrance, and some carrier accumulate and an outer surface or outer portion where the surfactant has accumulated. Odor-causing materials are absorbed through the outer (surfactant) layer into the core of the agglomeration resulting in a reduction of the vapor pressure and therefore odor reduction.

The examples disclosed above are micro emulsions of fragrance, TEG, ethanol and water. When applied, the micro emulsion penetrates into the spaces between fibers of a soft surface. Upon evaporation, most of the volatile components (water and ethanol) are removed and a residual agglomeration or droplet of TEG, ethanol, water, fragrance and surfactant serves as an absorbent for odor-causing compounds and molecules. The agglomerations also serve as fragrance extenders.

While only certain embodiments have been set forth, alternative embodiments and various modifications will be apparent from the above descriptions of those skilled in the art. These and other alternatives are considered equivalents and within the spirit and scope of this disclosure.

The invention claimed is:

1. A method for treating odors embedded in or adsorbed onto a soft surface, the method comprising:
   applying a liquid composition onto a soft surface wherein the composition comprises triethylene glycol (TEG) in an amount ranging from about 0.5 to about 5.0 wt %, a short chain monohydric alcohol, at least one nonionic surfactant comprising a hydrogenated castor oil derivative and at least one ionic surfactant; and
   allowing the composition to absorb into the soft surface and make contact with a malodorant disposed within the soft surface.

2. The method of claim 1 further comprising
   allowing the composition to form agglomerations within the soft surface;
   absorbing malodorants disposed in the soft surface into the agglomerations.

3. The method of claim 2 further comprising:
   allowing at some malodorant to desorb from the soft surface and enter an ambient gas phase.

4. The method of claim 2 wherein the composition further comprises a glycol ether.

5. The method of claim 2 wherein the ionic surfactant is a quaternary ammonium salt.

6. The method of claim 5 wherein the composition comprises from about 0.5 to about 1.5 wt % nonionic surfactant and from about 0.1 to about 1 wt % ionic surfactant.

7. The method of claim 6 wherein the nonionic surfactant further comprises a polyglycol ether.

8. The method of claim 1 wherein the alcohol is ethanol, the composition further comprises fragrance, the at least one nonionic surfactant further comprises a polyglycol ether, and the hydrogentated castor oil derivate and the polyglycol ether are present in a cumulative amount ranging from about 0.5 to about 1.5 wt %.

9. The method of claim 5 wherein the quaternary ammonium salt is present in an amount ranging from about 0.1 to about 1 wt %.

10. The method of claim 8 wherein the ethanol is present in an amount ranging from about 1 to about 10 wt %, the TEG is present in an amount ranging from about 0.5 to about 1.5 wt %; and the fragrance is present in an amount ranging from about 0.25 to about 0.75 wt %.

11. The method of claim 10 wherein the composition further comprises a quaternary ammonium salt.

12. A composition for treating odors in soft surfaces, the composition comprising:
   a short chain monohydric alcohol or a glycol ether present in an amount ranging from about 1 to about 10 wt %;
   triethylene glycol (TEG) present in an amount ranging from about 0.5 to about 5 wt %;
   at least one nonionic surfactant comprising a hydrogenated castor oil derivative present in an amount ranging from about 0.5 to about 1.5 wt %;
   at least one ionic surfactant comprising a quaternary ammonium salt present in an amount ranging from about 0.1 to about 1 wt %; and water.

13. The composition of claim 12 wherein the at least one nonionic surfactant further comprises a polyglycol ether.

14. A composition of claim 13 wherein the hydrogenated castor oil derivative is an ethoxylated hydrogenated castor oil and the polyglycol ether is a polyoxyethylene alkylether.

15. The composition of claim 12 wherein the TEG is present in an amount ranging from about 0.5 to about 1.5 wt %.

16. The composition of claim 12 wherein the alcohol is ethanol and is present in an amount ranging from about 1 to about 10 wt %;
   the TEG is present in an amount ranging from about 0.5 to about 1.5 wt %;
   the composition further comprises fragrance present in an amount ranging from about 0.25 to about 0.75 wt %; and the cumulative amount of the surfactants ranges from about 0.6 to about 2 wt %.

17. The composition of claim 16 wherein the surfactants further comprise at least one polyglycol ether.

18. A composition for treating odors embedded in or adsorbed onto soft surfaces, the composition comprising:
- from about 1 to about 10 wt % short chain monohydric alcohol;
- from about 0.5 to about 1.5 wt % TEG;
- from about 0.5 to about 1.5 wt % of at least one nonionic surfactant comprising a hydrogenated castor oil derivative;
- from about 0.1 to about 1 wt % of at least one ionic surfactant comprising a quaternary ammonium salt; and
- water.

19. A method for treating odors embedded in soft surfaces, the method comprising:
- applying a liquid composition according to claim 18 onto a soft surface,
- allowing the composition to absorb into the soft surface and make contact with a malodorant disposed within the soft surface;
- allowing the composition to form agglomerations within the soft surface; and
- absorbing malodorants disposed in the soft surface into the agglomerations.

* * * * *